United States Patent [19]
Sano et al.

[11] Patent Number: 4,850,711
[45] Date of Patent: Jul. 25, 1989

[54] FILM THICKNESS-MEASURING APPARATUS USING LINEARLY POLARIZED LIGHT

[75] Inventors: Kazuo Sano; Takao Miyazaki; Yoshiro Yamada, all of Tokyo, Japan

[73] Assignee: Nippon Kokan Kabushiki Kaisha, Tokyo, Japan

[21] Appl. No.: 62,242

[22] Filed: Jun. 11, 1987

[30] Foreign Application Priority Data

Jun. 13, 1986 [JP] Japan ................... 61-137458
Jul. 30, 1986 [JP] Japan ................... 61-179145

[51] Int. Cl.$^4$ ............................ G01B 11/06
[52] U.S. Cl. ...................... 356/382; 356/369
[58] Field of Search ........... 356/381, 382, 367, 369

[56] References Cited

U.S. PATENT DOCUMENTS

| | | | |
|---|---|---|---|
| 3,994,586 | 11/1976 | Sharkins et al. | 356/73 |
| 4,585,348 | 4/1986 | Chastang et al. | 356/369 |
| 4,589,776 | 5/1986 | Carver et al. | 356/367 |

FOREIGN PATENT DOCUMENTS

A0163466 12/1985 European Pat. Off. .

OTHER PUBLICATIONS

"Shingaku-Giho", vol. 82 OQE83-22.
Smith, *Surface Science*, vol. 56, No. 1, Jun. 1976, pp. 212-220.

*Primary Examiner*—F. L. Evans
*Attorney, Agent, or Firm*—Frishauf, Holtz Goodman & Woodward

[57] ABSTRACT

A linearly polarized light beam is applied to the surface of a film and is reflected therefrom. The beam is then split into three light beams by three or four optical flats. These light beams are applied to photoelectric conversion devices after passing through analyzers with fixed analyzing angles. The photoelectric conversion devices convert the beams into electric signals representing the intensities of these light beams. Two ellipsometric parameters $\psi$ and $\Delta$ are calculated from these three electric signals.

7 Claims, 8 Drawing Sheets

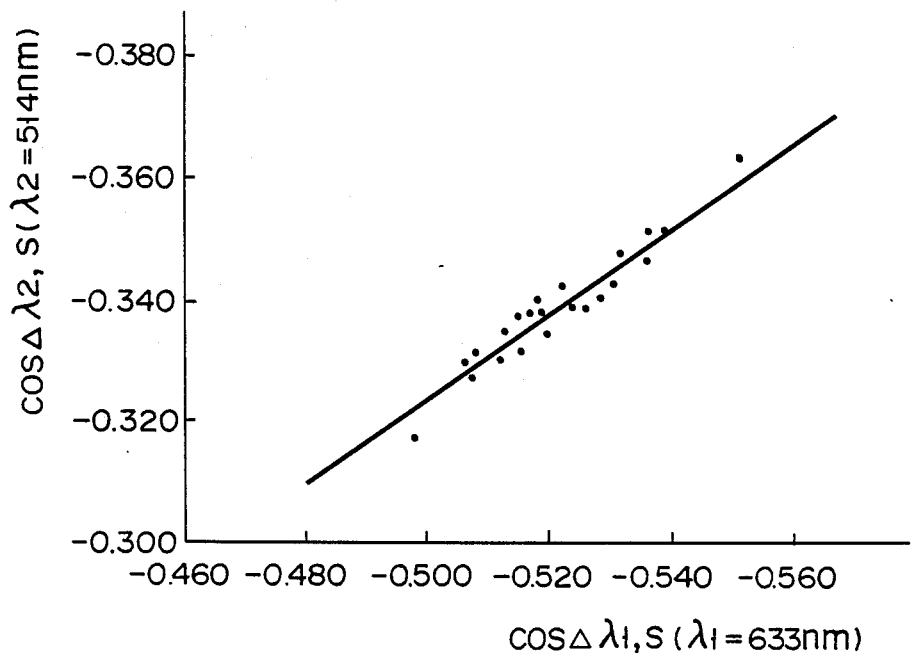
F I G. 10
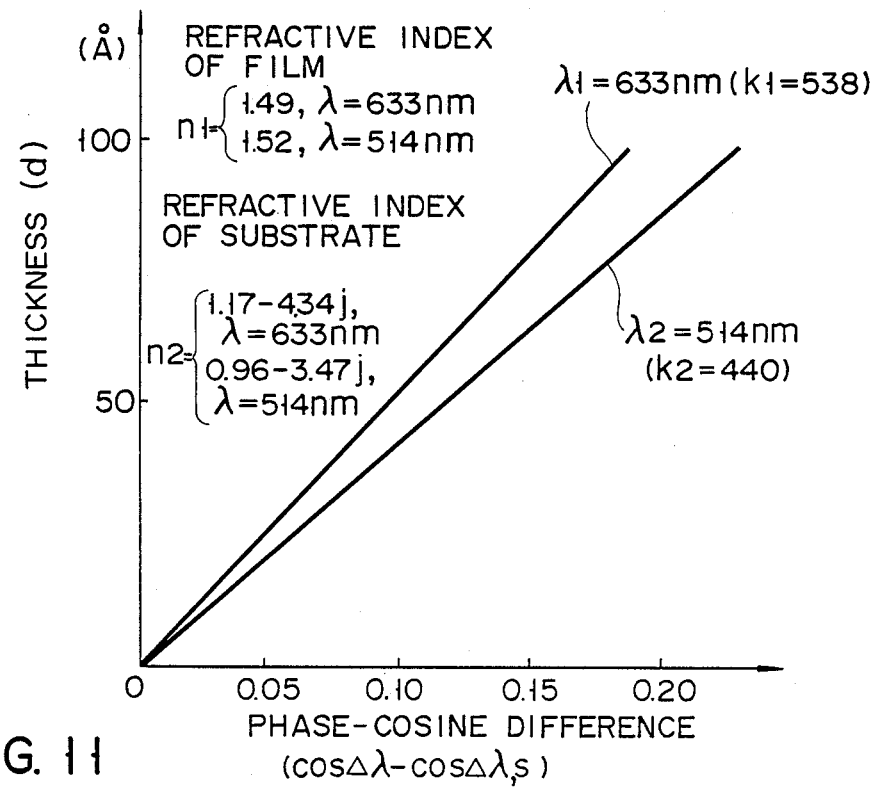
F I G. 11

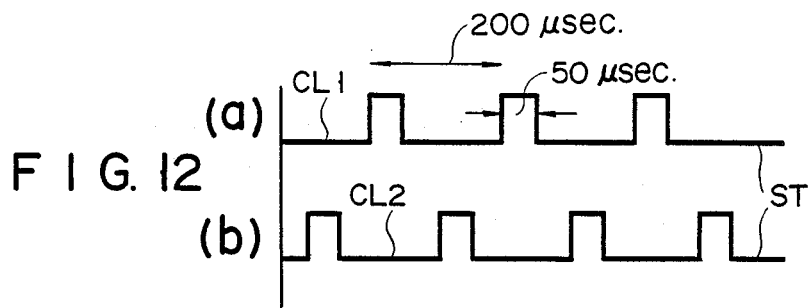
F I G. 12
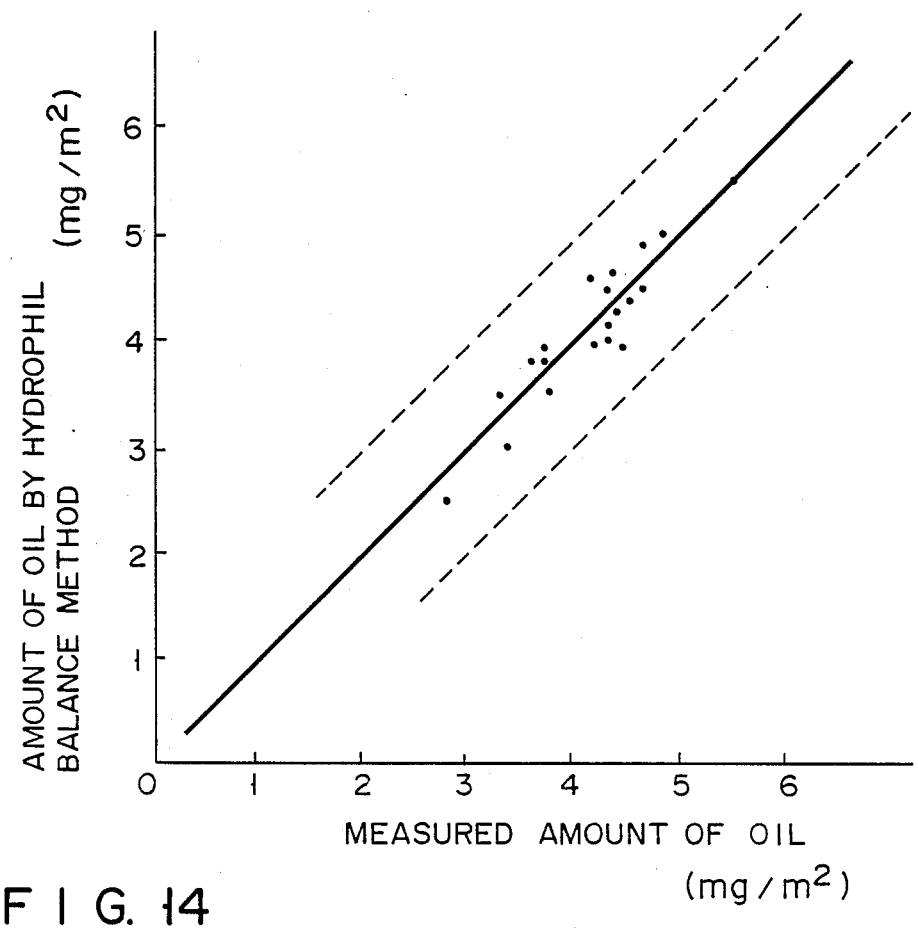
F I G. 14

FILM THICKNESS-MEASURING APPARATUS USING LINEARLY POLARIZED LIGHT

BACKGROUND OF THE INVENTION

The present invention relates to a film thickness-measuring apparatus which is fit for on-line measuring of the thickness of an oil film coated on the surface of a steel plate being processed in, for example, a rolling line or a plating line, and which can measure the thickness of the oil film without contacting the oil film.

The ellipsometry method is generally known as a method of measuring the thickness of a light-transmitting film such as an oil film coated on the surface of a steel plate. This method is based on the fact that the difference in state of polarization between the light reflected from the substrate steel plate with oil film coating and the light reflected from the steel plate without any coating is closely related to the thickness of the oil film. More specifically, thickness d of the oil film can be calculated from the ratio $\rho$ of the Fresnel complex amplitude reflection coefficient $(r_p)$ of the p component of the reflected light, which is parallel to the plane of incidence, to the Fresnel complex amplitude reflect on coefficient $(r_s)$ of the s component of the reflected light, which is perpendicular to the plane of incidence. Ratio $\rho$ (hereinafter called "reflection coefficient ratio") has the following relation with ellipsometric parameters $\psi$ and $\Delta$ which serve to determine thickness d:

$$\rho = r_p/r_s = \tan\psi \exp^{j\Delta} \tag{1}$$

Ellipsometric parameters $\psi$ and $\Delta$, thickness d, refractive index $N_1$ of the oil film, refractive index $N_2$ of the steel plate, incidence angle $\phi_0$ of the light applied to the surface of the oil film, and wavelength $\lambda$ of the applied light have a relationship which can be given as:

$$\rho = F(d, N_1, N_2, \phi_0, \lambda) \tag{2}$$

Hence, thickness d can easily be calculated from parameters $\psi$ and $\Delta$.

Some methods of obtaining ellipsometric parameters $\psi$ and $\Delta$ are known. One of them is to apply elliptically polarized light generated through a compensator and a polarizer to the surface of a film whose thickness need be measured, and detect the light reflected from the layer after the light is passed through an analyzer. The analyzer and polarizer are rotated in the plane at right angles to the axis of the reflected light beam, until the analyzer passes no light at all. The angles through which the analyzer and polarizer have been rotated are then measured. Finally, ellipsometric parameters $\psi$ and $\Delta$ are obtained from the polarizing angle and the analyzing angle.

A method of obtaining ellipsometric parameter $\Delta$ is known. In this method, an analyzer of the same type as described above is rotated at high speed by an electric motor, the amount of the light passing through the analyzer is modulated with the number of rotations per unit time of the analyzer, and a photoelectric output is thereby produced. The photoelectric output, thus produced, has a component which represents ellipsometric parameter $\Delta$. Hence, parameter $\Delta$ can be obtained from the photoelectric output.

The first-mentioned method has a drawback, however. It takes a few seconds to adjust the orientations of the polarizer and the analyzer so that no light is transmitted through them. Therefore, this method cannot accurately measure the thickness of the layer in the case where the film is moving fast.

The second-mentioned method is also disadvantageous. The ellipsometric parameter, $\Delta$, depends to a significant extent on the reflection coefficient of the film, the amount of the light emitted from a light source, and some other similar factors. Hence, parameter $\Delta$ obtained by this method cannot be so reliable. Furthermore, this method can provide only parameter $\Delta$, which is just one of the two ellipsometric parameters. Therefore, the method cannot be applied to other uses than thickness-measuring, such as measuring of the refractive index of the film.

SUMMARY OF THE INVENTION

It is accordingly the object of the present invention to provide a film thickness-measuring apparatus for accurately measuring the thickness of a film coated on an object moving at high speed, without contacting the film.

According to the present invention, there is provided a film thickness-measuring apparatus, wherein a beam of linearly polarized light, with a prescribed polarization angle, is applied to the surface of a film at a predetermined angle of incidence, thereby to measure the thickness of the film. The beam reflected from the film is split by a beam splitter into a plurality of beams. These beams are made to pass through a plurality of analyzers having different analyzing angles. Electric signals are then generated which are at different levels proportionate to the intensities of the polarized light beams which have passed through the analyzers. These signals are supplied to a signal-processing section. This section processes the electric signals, thereby calculates both ellipsometric parameters, that is, amplitude ratio $\psi$ and phase $\Delta$.

BRIEF DESCRIPTION OF THE DRAWINGS

FIG. 10 is a graph representing the relationship between the phase-cosines of the light beam reflected from the substrate for two wavelengths;

FIG. 11 is a graph illustrating the relationship between the thickness of a film and the phase cosine difference;

FIG. 12 is a timing chart showing two shutter drive signals;

FIG. 14 is a graph representing the relationship between the amount of oil applied to the surface of an object and the measured thickness of the oil film coated on the object.

DETAILED DESCRIPTION OF THE PREFERRED EMBODIMENTS

A few embodiments of the present invention will now be described in detail with reference to the drawings attached hereto.

Figure 1:
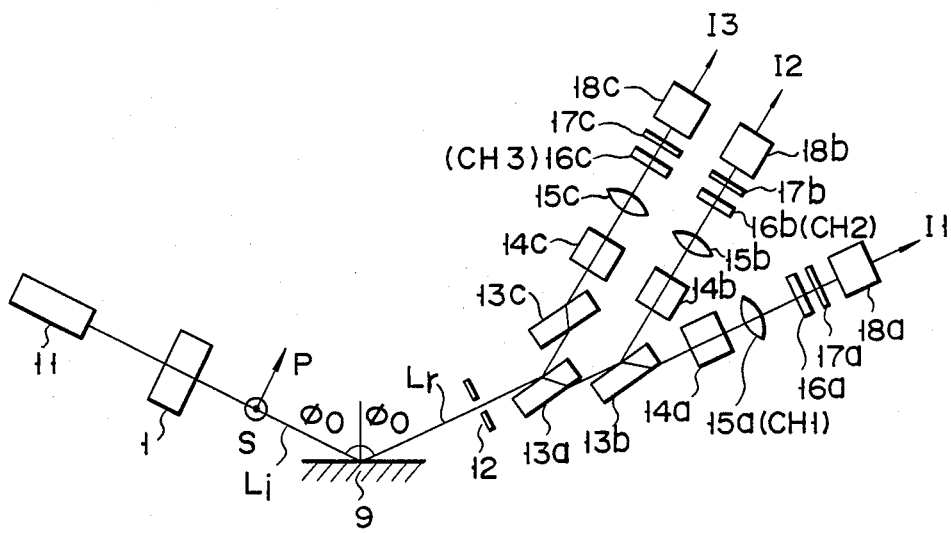
FIG. 1 is a block diagram showing the optical system of a first embodiment of the present invention.
Figure 2:
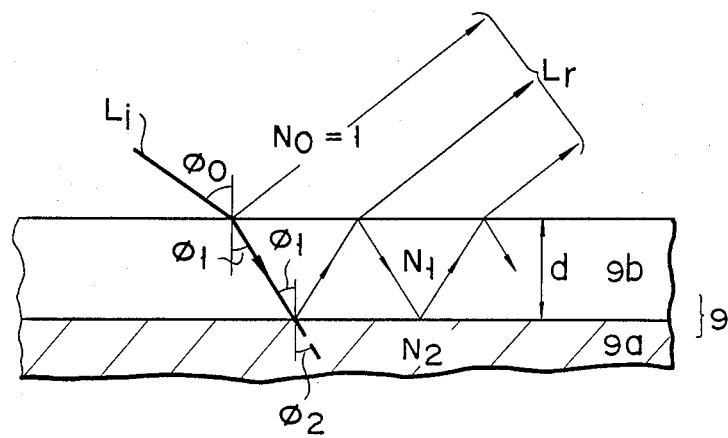
FIG. 2 is an enlarged view of that portion of a film to which a beam of linearly polarized light is applied to measure the thickness of the film.
Figure 3:
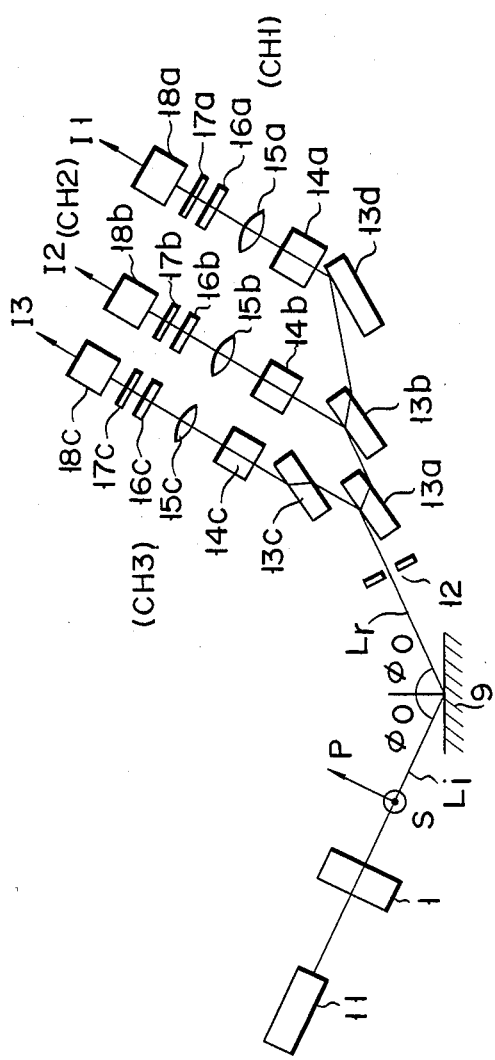
FIG. 3 is a block diagram showing the optical system of a modified embodiment of the present invention.
Figure 4:
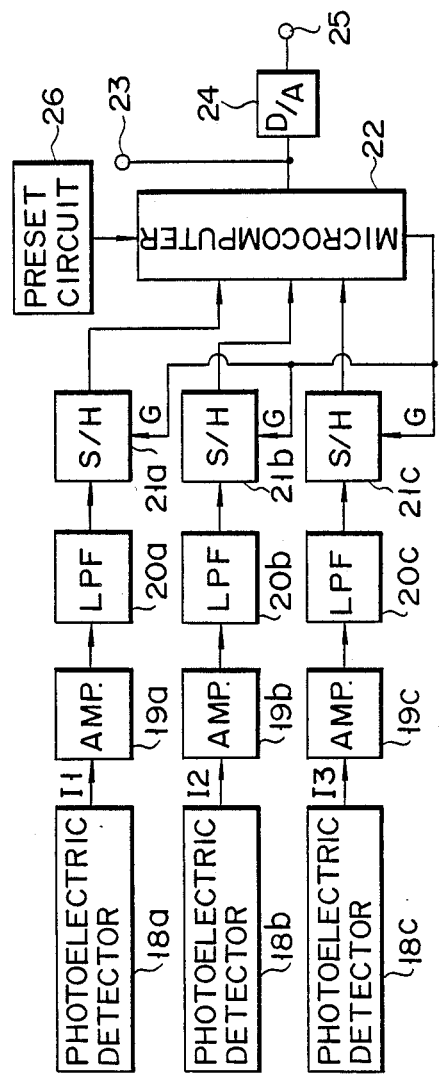
FIG. 4 is a block diagram showing the signal-processing section used in the first embodiment.

FIGS. 1 to 5 show a first embodiment of the invention. FIG. 1 schematically illustrates the optical system of this embodiment. FIG. 4 is a block diagram showing the signal-processing section of the embodiment. As is shown in FIG. 1, monochromatic light source 11 emits a collimated, monochromatic light. This monochromatic light is applied to polarizer 1. Polarizer 1 converts the light to a linearly polarized light $L_i$ having a prescribed orientation angle $\theta$. Polarized light $L_i$ is applied to object 9 at an incidence angle $\phi_0$.

As is shown in FIG. 2, object 9 consists of steel plate 9a and oil film 9b coated on one surface of plate 9a. In this instance, polarized light $L_i$ is applied to object 9 to measure the thickness of oil film 9b. (According to the invention, oil film 9b can be replaced by a resin film, a semiconductor oxide film, or a metal film, whose thickness will be measured.) The air, to which oil film 9b is exposed, has refractive index $N_0$ (=1), oil film 9b has refractive index $N_1$, and steel plate 9a has refractive index $N_2$. Let us assume that oil film 9b has thickness d. Light $L_i$ applied to the surface of oil film 9b at incidence angle $\phi_0$ is refracted in oil film 9b, and is thus incident on the surface of steel plate 9a at angle $\phi_1$. Light $L_i$ is then reflected from the surface of plate 9a and passes through oil film 9b. It finally emerges out of oil film 9b, as reflected light $L_r$.

Let us assume that polarized light $L_i$ is applied along a Z axis within the plane of incidence, which is parallel to the drawing of FIG. 1. The S axis is defined orthogonal to the plane of incidence, the P axis orthogonal to both Z axis and S axis, so that the P axis, S axis, and Z axis define a right-handed Cartesian coordinate system.

Light $L_r$ reflected from object 9 at reflection angle $\phi_0$ passes through aperture 12, and thereby changes to a light beam having a controlled diameter. This light beam is split into three beams by three optical flats 13a, 13b and 13c which are made of the same material and have the same shape. These optical flats 13a, 13b and 13c constitute a beam-splitting section. They are made of transparent, optically isotropic material, spaced apart from one another, and positioned parallel to one another. The thickness of optical flats 13a, 13b and 13c, and the distances between them are determined such that none of these optical flats emits multiplex reflected light.

The light beam passing through optical flats 13a and 13b propagates in beam channel ch1. The light beam reflected by optical flat 13b propagates in beam channel ch2, and the light beam reflected by optical flat 13a propagates in beam channel ch3. Beam channels ch2 and ch3 are parallel to each other. In beam channel ch1, analyzer 14a, focusing lens 15a, aperture 16a, interference filter 17a, and photoelectric detector 18a are provided. In beam channel ch2, analyzer 14b, focusing lens 15b, aperture 16b, interference filter 17b, and photoelectric detector 18b are provided. Similarly, in beam channel ch3, analyzer 14c, focusing lens 15c, aperture 16c, interference filter 17c, and photoelectric detector 18c are provided. Analyzers 14a, 14b and 14c have specific orientation angles $\alpha_1$, $\alpha_2$ and $\alpha_3$. Focusing lenses 15a, 15b and 15c have the same focal distance. Apertures 16a, 16b and 16c are located at the focal points of focusing lenses 15a, 15b and 15c, respectively. Interference filters 17a, 17b and 17c remove the light which has externally entered the optical system. Photoelectric detectors 18a, 18b and 18c convert the output beams from filters 17a, 17b and 17c into electric signals $I_1$, $I_2$ and $I_3$ which represent the intensities of these light beams. Signals $I_1$, $I_2$ and $I_3$ undergo predetermined processings in the signal-processing section shown in FIG. 4, thereby to provide ellipsometric parameters $\psi$ and $\Delta$, from which thickness d of oil film 9b will be calculated.

As is shown in FIG. 4, electric signals $I_1$, $I_2$ and $I_3$ output from photoelectric detectors 18a, 18b and 18c are amplified by amplifiers 19a, 19b and 19c, and are then supplied to low-pass filters 20a, 20b and 20c. Low-pass filters 20a, 20b and 20c remove noise from the output signals of amplifiers 19a, 19b and 19c. The output signals of low-pass filters 20a, 29b and 20c are input to sample-and-hold circuits (hereinafter called "S/H circuits") 21a, 21b and 21c. S/H circuits 21a, 21b and 21c sample and hold the output signals of beam channels ch1, ch2 and ch3 simultaneously, by using a gate signal G supplied from microcomputer 22. Hence, output signals $I_1$, $I_2$ and $I_3$ of channels ch1, ch2 and ch3 are input to microcomputer 22 at the same time. Microcomputer 22 processes signals $I_1$, $I_2$ and $I_3$ as will be explained below, thereby providing digital data representing the thickness d of oil film 9b. The digital data is output from microcomputer 22 via output terminal 23. It is also input to D/A converter 24 and converted to analog signal. The analog signal, thus provided, is output from output terminal 25. Output terminal 25 is connected to a chart recorder (not shown). Preset circuit 26 is connected to microcomputer 22, for inputting gains for channels ch1, ch2 and ch3, the value of $\Phi_0$, $|\sigma_1 \sigma_2|$ and minimum light intensity $I_{3min}$ to microcomputer 22.

Microcomputer 22 processes output signals $I_1$, $I_2$ and $I_3$ of channels ch1, ch2 and ch3, by using the Jones matrix method, in order to calculate ellipsoparameters $\psi$ and $\Delta$. These parameters can is defined by the following equation:

$$r_p/r_s = \tan\psi e^{j\Delta} \quad (3)$$

where $r_p$ is the Fresnel complex amplitude-reflection coefficient of the electric vector of the P component of polarized light $L_i$, and $r_s$ is the Fresnel complex amplitude-reflection coefficient of the electric vector of the S component of polarized light $L_i$.

Ratio $\sigma_1$ of the Fresnel complex amplitude-transmission coefficient $t_s'$ of the S component of reflected light $L_r$ applied to each optical flat to the Fresnel complex amplitude-transmission coefficient $t_p'$ of the P component of the same light $L_r$ is given by equation (4). Ratio $\sigma_2$ of the Fresnel complex amplitude-reflection coefficient $r_s'$ of the S component of reflected light $L_r$ applied to each optical flat to the Fresnel complex amplitude-reflection coefficient $r_p'$ of the P component of light $L_r$ is given by equation (5).

$$\sigma_1 = t_s'/t_p' = |\sigma_1|e^{j\Phi_1} \quad (4)$$

$$\sigma_2 = r_s'/r_p' = |\sigma_2|e^{j\Phi_2} \quad (5)$$

where $\Phi_1$ is the phase of ratio $\sigma_1$, and $\Phi_2$ is the phase of ratio $\sigma_2$. Hence, the phase difference between $\sigma_1$ and $\sigma_2$ can be given:

$$\Phi_0 = \Phi_1 - \Phi_2 \tag{6}$$

Amplitude-reflectivity $r_s$ and $r_p$, both in equation (3), are given in the form of the Fresnel reflection coefficient, which is represented by the following formula:

$$r_{s,p} = \frac{(r_{01})_{s,p} + (r_{12})_{s,p} \, exp^{-j2\beta}}{1 + (r_{01})_{s,p} \, (r_{12})_{s,p} \, exp^{-j2\beta}}$$

Therefore, the S component, $(r_{kl})s$, and the P component, $(r_{kl})p$, are given:

$$(r_{kl})p = \frac{N_l \cos\phi_k - N_k \cos\phi_l}{N_l \cos\phi_k + N_k \cos\phi_l}$$

$$(r_{kl})s = \frac{N_l \cos\phi_k - N_k \cos\phi_l}{N_k \cos\phi_k - N_l \cos\phi_l}$$

where $$2\beta = \frac{4\pi}{\lambda} dN_1 \cos\phi_1$$

$$\sin\phi_0 = N_1 \sin\phi_1 = N_2 \sin\phi_2$$

In the equation showing $2\beta$, $\lambda$ represents the wavelength of polarized light $L_i$.

From the equations given above, signals $I_1$, $I_2$ and $I_3$, which represent the intensities of the light beams output from channels ch1, ch2 and ch3 after signal processing, are given as follows:

$$I_1 = K_1 \tau_1 |r_s|^2 |t_p'|^4 I_0 \{\tan^2\psi \cos^2\alpha_1 \cos^2\theta + \tag{7}$$
$$2\tan\psi |\sigma_1|^2 \sin\alpha_1 \cos\alpha_1 \cos\theta \sin\theta \cos(\Delta - 2\Phi_1) +$$
$$|\sigma_1|^4 \sin^2\alpha_1 \sin^2\theta\}$$

$$I_2 = \tag{8}$$
$$K_2 \tau_2 |r_s|^2 |t_p'|^2 |r_p'|^2 I_0 \{\tan^2\psi \cos^2\alpha_2 \cos^2\theta +$$
$$2\tan\psi |\sigma_1 \sigma_2| \sin\alpha_2 \cos\alpha_2 \cos\theta \sin\theta \cos(\Delta - \Phi_0) +$$
$$|\sigma_1 \sigma_2|^2 \sin^2\alpha_2 \sin^2\theta\}$$

$$I_3 = \tag{9}$$
$$K_3 \tau_3 |r_s|^2 |t_p'|^2 |r_p'|^2 I_0 \{\tan^2\psi \cos^2\alpha_3 \cos^2\theta +$$
$$2\tan\psi |\sigma_1 \sigma_2| \sin\alpha_3 \cos\alpha_3 \cos\theta \sin\theta \cos(\Delta - \Phi_0) +$$
$$|\sigma_1 \sigma_2|^2 \sin^2\alpha_3 \sin^2\theta\}$$

In equations (7), (8) and (9), $K_1$, $K_2$ and $K_3$ are the gains of the amplification circuits 19a, 19b, 19c for channels ch1, ch2 and ch3, $\tau_1$, $\tau_2$ and $\tau_3$ are the light-transmitances of analyzers 14a, 14b and 14c and photoelectric detectors 18a, 18b and 18c for channels ch1, ch2 and ch3, $I_0$ is the intensity of polarized light $L_i$ incident on oil film 9b, $\theta$ is the polarizing angle of polarizer 1, and $\alpha_1$, $\alpha_2$ and $\alpha_3$ are the analyzing angles of analyzers 14a, 14b and 14c for beam channels ch1, ch2 and ch3.

Gains $K_1$, $K_2$ and $K_3$ for channels ch1, ch2 and ch3 are adjusted such that photoelectric detectors 18a, 18b and 18c output signals $I_1$, $I_2$ and $I_3$ have an equal value for any object, ($I_G \tan^2\psi_0 \cos^2\theta_0$), when the orientation angle of polarizer 1 has value $\theta_0$ other than 90° and the orientation angles $\alpha_1$, $\alpha_2$ and $\alpha_3$ of optical detectors 14a, 14b and 14c are set at 0°. Hence, $$K_1 \tau_1 |r_s|^2 |t_p'|^4 I_0 \cos^2\theta_0 \tan^2\psi_0 = \tag{10}$$
$$K_2 \tau_2 |r_s|^2 |t_p'|^2 |r_p'|^2 I_0 \cos^2\theta_0 \tan^2\psi_0 =$$
$$K_3 \tau_3 |r_s|^2 |t_p'|^2 |r_p'|^2 I_0 \cos^2\theta_0 \tan^2\psi_0 =$$
$$I_G \cos^2\theta_0 \tan^2\psi_0$$

Using equation (10), we can change equations (7), (8) and (9) to the following:

$$I_1 = I_G \{\tan^2\psi \cos^2\alpha_1 \cos^2\theta + \tag{7'}$$
$$2\tan\psi |\sigma_1|^2 \sin\alpha_1 \cos\alpha_1 \cos\theta \sin\theta \times$$
$$\cos(\Delta - 2\Phi_1) + |\sigma_1|^4 \sin^2\alpha_1 \sin^2\theta\}$$

$$I_2 = I_G \{\tan^2\psi \cos^2\alpha_2 \cos^2\theta + \tag{8'}$$
$$2\tan\psi |\sigma_1 \sigma_2| \sin\alpha_2 \cos\alpha_2 \cos\theta \sin\theta \times$$
$$\cos(\Delta - \Phi_0) + |\sigma_1 \sigma_2|^2 \sin^2\alpha_2 \sin^2\theta\}$$

$$I_3 = I_G \{\tan^2\psi \cos^2\alpha_3 \cos^2\theta + \tag{9'}$$
$$2\tan\Psi |\sigma_1 \sigma_2| \sin\alpha_3 \cos\theta \sin\theta \times$$
$$\cos(\Delta - \Phi_0) + |\sigma_1 \sigma_2|^2 \sin^2\alpha_3 \sin^2\theta\}$$

When polarizer 1 has orientation angle $\theta$ of 45°, and optical detectors 14a, 14b and 14c have orientation angle $\alpha_1$ of 0°, orientation angle $\alpha_2$ to 45°, and orientation angle $\alpha_3$ of −45°, output signals $I_1$, $I_2$ and $I_3$ of beam channels ch1, ch2 and ch3 will be given as follows:

$$I_1 = \frac{1}{2} I_G \tan^2\psi \tag{11}$$

$$I_2 = \frac{1}{4} I_G \{\tan^2\psi + 2\tan\psi |\sigma_1 \sigma_2| \times \tag{12}$$
$$\cos(\Delta - \Phi_0) + |\sigma_1 \sigma_2|^2\}$$

$$I_3 = \frac{1}{4} I_G \{\tan^2\psi - 2\tan\psi |\sigma_1 \sigma_2| \times \tag{13}$$
$$\cos(\Delta - \Phi_0) + |\sigma_1 \sigma_2|^2\}$$

From equations (11), (12) and (13), we can obtain:

$$\cos(\Delta - \Phi_0) = \frac{I_2 - I_3}{2 I_1} \sqrt{\frac{I_1}{I_2 + I_3 - I_1}} \tag{14}$$

$$\tan\psi = |\sigma_1 \sigma_2| \sqrt{\frac{I_1}{I_2 + I_3 - I_1}} \tag{15}$$

Both $\Phi_0$ and $|\sigma_1 \sigma_2|$ are invariables which are specific to optical flats 13a, 13b and 13c. Therefore, when a linearly polarized light beam having orientation angle $\theta_0$ is applied to the beam-splitting section, these invariables $\Phi_0$ and $|\sigma_1 \sigma_2|$ are given as follows from output signals $I_{1,0}$ $I_{2,0}$ and $I_{3,0}$ obtained in this instance:

$$\Phi_0 = \arccos\left[\frac{I_{2,0} - I_{3,0}}{2 I_{1,0}} \sqrt{\frac{I_{1,0}}{I_{2,0} + I_{3,0} - I_{1,0}}}\right] \tag{16}$$

$$|\sigma_1 \sigma_2| = \tan\theta_0 \sqrt{\frac{I_{2,0} + I_{3,0} - I_{1,0}}{I_{1,0}}} \quad (17)$$

In the case where a glass plate, whose refractive index n is known, is being measured $\Phi_0$ and $|\sigma_1 \sigma_2|$ can be given as follows from output signals $I_1$, $I_2$ and $I_3$:

$$\Phi_0 = \arccos\left[\frac{I_2 - I_3}{2I_1} \sqrt{\frac{I_1}{I_2 + I_3 - I_1}}\right] \quad (18)$$

$$|\sigma_1 \sigma_2| = \frac{\sin^2 \phi_0 - \cos\phi_0 \sqrt{n^2 - \sin^2 \phi_0}}{\sin^2 \phi_0 + \cos\phi_0 \sqrt{n^2 - \sin^2 \phi_0}} \cdot \quad (19)$$

$$\sqrt{\frac{I_2 + I_3 - I_1}{I_1}}$$

In equation (19), $\phi_0$ represents the incidence angle of polarized light $L_i$. Hence, ellipsometric parameters $\psi$ and $\Delta$ can be simultaneously obtained by substituting these values for invariables $\Phi_0$ and $|\sigma_1 \sigma_2|$, in (14) and (15). In fact, invariable $\Phi_0$ is very small, nearly equal to 0°, and invariable $|\sigma_1 \sigma_2|$ is determined by the incidence angle $\phi_0$ of polarized light $L_i$, and takes the value of about 2 when angle $\phi_0$ is 70°.

Since, as is evident from equations (14) and (15), both $\cos(\Delta - \Phi_0)$ and $\tan\psi$ are obtained from output signals $I_1$, $I_2$ and $I_3$ in a dimensionless form, and signals $I_1$, $I_2$ and $I_3$ are simultaneously produced, $\cos(\Delta - \Phi_0)$ and $\tan\psi$ are not influenced by the changes in the intensity of reflected light $L_r$ which have resulted from the changes in the intensity of the light emitted from light source 11.

As long as $\phi \neq 0°$ or 90°, $\alpha_1 = 0°$, $\alpha_2 = -\alpha_3$ ($\alpha_2 \neq 0$, 90°) are maintained $\psi$ and $\Delta$ can also be obtained. In this case, equations (14) and (15) are changed to the following:

$$\cos(\Delta - \Phi_0) = \frac{(I_2 - I_3)}{2\sqrt{2}\cos\alpha_2 I_1} \sqrt{\frac{I_1}{I_2 + I_3 - 2\cos^2\alpha_2 I_1}} \quad (20)$$

$$\tan\psi = \sqrt{2} \, |\sigma_1 \sigma_2| \sin\alpha_2 \tan\theta \sqrt{\frac{I_1}{I_2 + I_3 - 2\cos^2\alpha_2 I_1}} \quad (21)$$

Apertures 16a, 16b and 16c are provided in front of photoelectric detectors 18a, 18b and 18c in order to eliminate a measuring error due to the inclination of object 9. More specifically, apertures 16a, 16b and 16c reduce the angle of view to ±0.2° or less. This is because the measuring error will amount to as much as tens of angstroms when object 9 is inclined by 1.0°. The angle of view can be reduced to said value when the apertures 16a, 16b and 16c have diameter D given below:

$$D \leq 7.0 \times 10^{-3} f \quad (22)$$

where f is the focal distance of focusing lenses 15a, 15b and 15c. Therefore, when sample 9 is inclined by 0.2° or more, reflected light $L_r$ is partly shielded by apertures 16a, 16b and 16c, whereby signals $I_1$, $I_2$ and $I_3$ fall to a lower level. One of these electric signals, signal $I_3$, for example, is monitored, and the minimum light intensity $I_{3min}$ is preset by operating preset circuit 26. Whenever signal $I_3$ is at a level lower than $I_{3min}$, none of signals $I_1$, $I_2$ and $I_3$ are used in calculating thickness d of oil film 9b. This measure taken, the reliability of photoelectric detectors 18a, 18b and 18c are maintained at 99% or more, and the measuring error of the apparatus can be reduced to ±5 Å.

Figure 5:
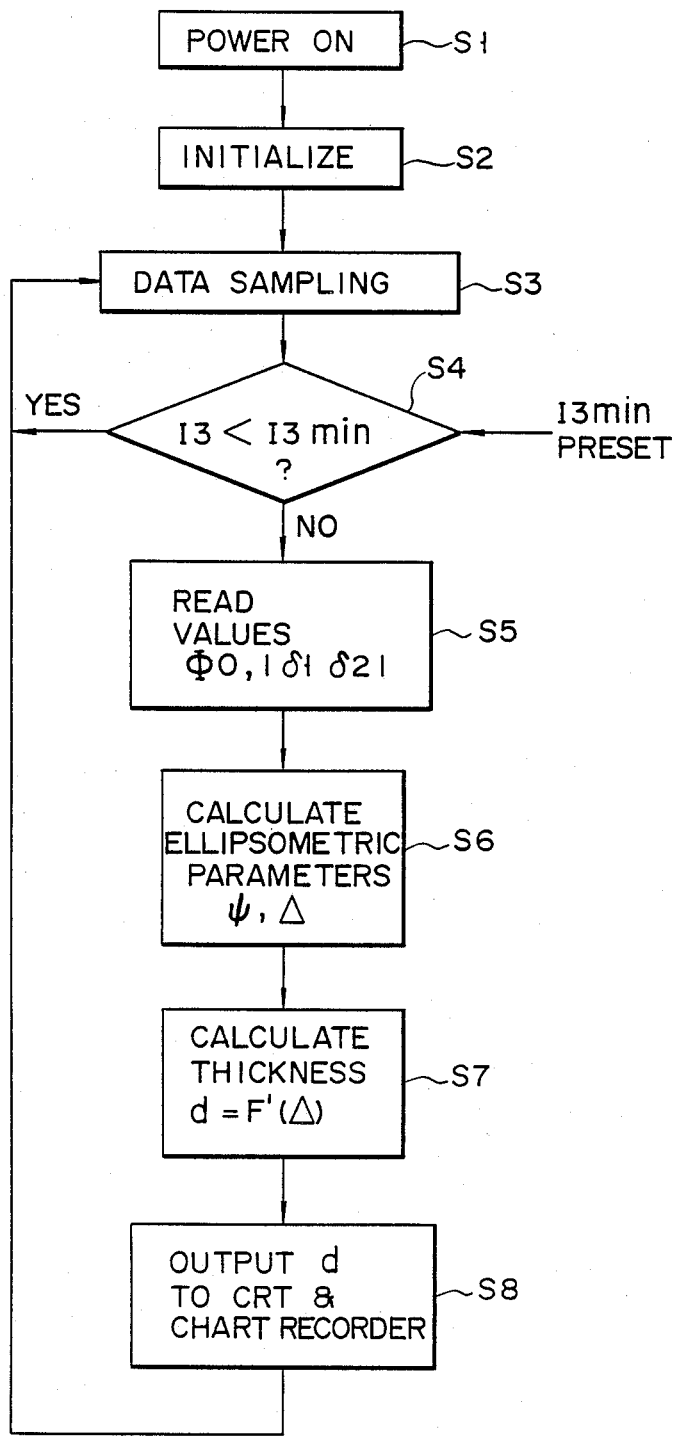
FIG. 5 is a flow chart explaining the step performed by the microcomputer in FIG. 4.

The operation of microcomputer 22 will now be explained with reference to the flow chart of FIG. 5. When the power switch (not shown) of the apparatus is turned on in step S1, light source 11 (FIG. 1) is turned on and starts emitting monochromatic light. At the same time, all components of the circuit shown in FIG. 4 are energized. In the next step, S2, microcomputer 22 is initialized and then outputs gate signals $G_1$, $G_2$ and $G_3$. Gate signals $G_1$, $G_2$ and $G_3$ are supplied to S/H circuits 21a, 21b and 21c, thus clearing these S/H circuits. At the same time, channel gains, $\Phi_0$, $|\sigma_1 \sigma_2|$, and $I_{3min}$ are preset by preset circuit 26.

When the initialization of microcomputer 22 is completed, the operation goes to step S3. In step S3, S/H circuits 21a, 21b and 21c sample signals $I_1$, $I_2$ and $I_3$, which have been output from beam channels ch1, ch2 and ch3, in response to gate signals $G_1$, $G_2$ and $G_3$. Then, in step S4, minimum light intensity $I_{3min}$ is compared with signal $I_3$ held by S/N circuit 21c. If $I_3 < I_{3min}$, sampled signals $I_1$, $I_2$ and $I_3$ are not valid for calculating thickness d of oil film 9b. In this case, the operation returns to step S3, in which S/H circuits 21a, 21b and 21c sample signals $I_1$, $I_2$ and $I_3$ again. If $I_3 \geq I_{3min}$, sampled signals $I_1$, $I_2$ and $I_3$ can be used to calculate thickness d of oil film 9b. In this case, signals $I_1$, $I_2$ and $I_3$ are input to microcomputer 22. Signals $I_1$, $I_2$ and $I_3$ which are represented by equations (11), (12) and (13), are processed by microcomputer 22 in accordance with equations (14) and (15), more precisely in accordance with the programs stored in microcomputer 22.

More specifically, in step S5, invariables $\Phi_0$ and $|\sigma_1 \sigma_2|$ both specific to optical flats 13a, 13b and 13c, are read out from a memory provided within microcomputer 22. In step S6, the calculations identical to equations (14) and (15) are performed, thereby obtaining ellipsometric parameters $\psi$ and $\Delta$. These parameters are used in step S7 according to equation in which a calculation (2), is carried out, thus obtaining thickness d of oil film 9b. The data representing thickness d is converted into analog data by D/A converter 24. In the next step, S8, this data is input to the cathode ray tube (not shown) or the chart recorder (not shown, either). Then, the operation returns to step S3.

The apparatus can obtain both ellipsometric parameters $\psi$ and $\Delta$ and also thickness d of oil film 9b, substantially in real time though with an extremely short time lag corresponding to the response time of photoelectric detectors 18a, 18b and 18c. Therefore, no noticeable time lags occur in measuring thickness d even if object 9 moves at 5 m/sec or more.

All components of the optical system, which are essential to the measuring accuracy, are fixed. The apparatus requires no movable mechanical parts. Nor does it need Faraday elements, or magnetoelectric polarizing elements such as KDP elements. The apparatus can, therefore, be simple in structure, have satisfactory mechanical strength, and be free of the influence from temperature changes. In addition, since values, $\cos(\Delta - \Phi_0)$ and $\tan\psi$ are obtained as a ratio of light intensities, the measuring accuracy is not affected by changes in the intensity of polarized light $L_i$ applied to object 9. Further, since the angle of view of photoelectric detectors 18a, 18b and 18c is reduced to 0.2° or less, the influence of the inclination of object 9 on the measuring accuracy can be minimized.

The present invention is by no means limited to the embodiment described above. In the embodiment of FIG. 3, instead of the three optical flats 13a, 13b and 13c in FIG. 1, four optical flats 13a, 13b, 13c and 13d made of the same material and having the same shape are placed parallel to one another to obtain 3 beams.

Since the 3 beams are parallel to one another, the alignment of the optics becomes considerably easy, and since the 3 beams are all reflected once on one of the optical flats, the power detected by detectors, 18a, 18b and 18c becomes nearly the same level.

Figure 6:
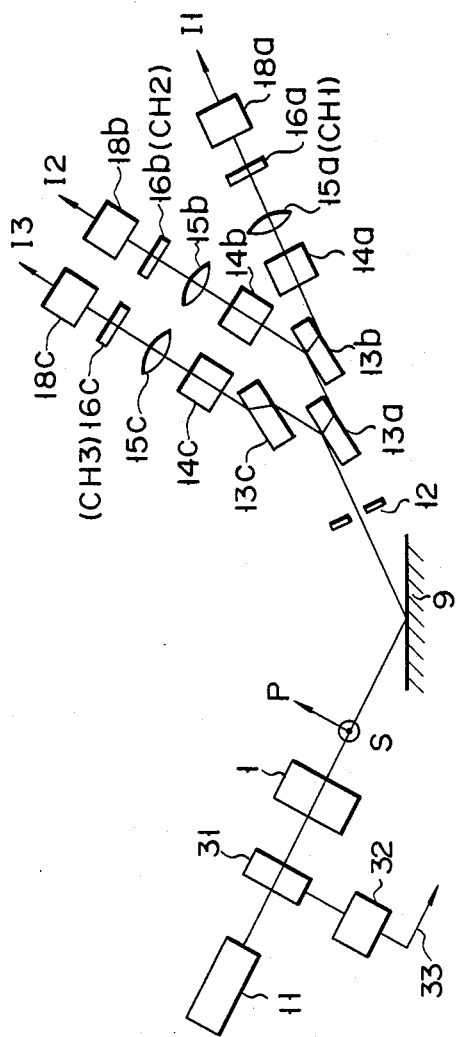
FIG. 6 is a block diagram showing the optical system used in a second embodiment of the invention.
Figure 7:
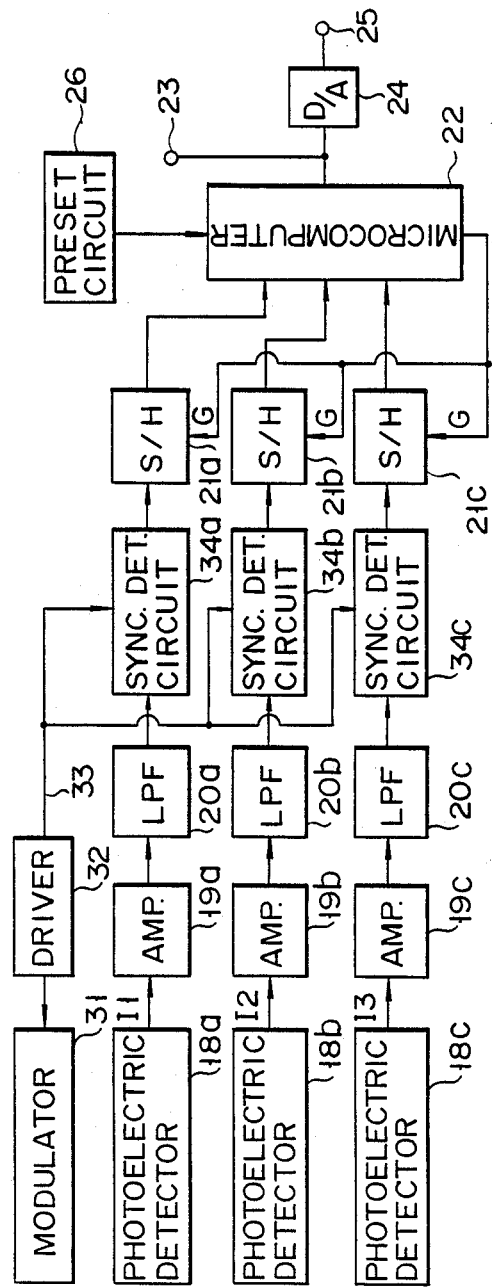
FIG. 7 is a block diagram of the circuit incorporated in the second embodiment.

In the embodiment of FIG. 1, interference filters 17a, 17b and 17c remove the light which has externally entered the optical system. As shown in FIG. 6, these filters 17a, 17b and 17c can be replaced by modulator 31 such as a chopper, which is interposed between light source 11 and polarizer 1, and drive circuit 32 for driving this modulator 31. When it is driven by circuit 32, modulator 31 modulates the monochromatic light emitted from light source 11, thereby removing the externally applied light from the monochromatic light upon demodulation. In this instance, it is necessary to supply modulation-reference signal 33, from drive circuit 32 to synchronous detector circuits 34a, 34b and 34c, as is illustrated in FIG. 7, thereby to detect the output signals of beam channels ch1, ch2 and ch3 in synchronism with the modulation.

In the embodiment shown in FIGS. 1 and 4, the normals of optical flats 13a, 13b and 13c exist in the incident plane. Nontheless, the apparatus can measure thickness d of oil film 9b even if optical flats 13a, 13b and 13c are positioned such that their normals are perpendicular to the incident plane. If this is the case, light $L_r$ will be reflected from flats 13a, 13b and 13c in the horizontal direction, that is, in the direction perpendicular to the drawing of FIG. 1, and the polarization plane is rotated 90°. Hence, equations (14) and (15) are changed to the following:

$$\cos(\Delta + \Phi_0) = \frac{I_2 - I_3}{2I_1} \sqrt{\frac{I_2 + I_3 - I_1}{I_1}} \quad (23)$$

$$\tan\psi = \frac{1}{|\sigma_1 \sigma_2|} \sqrt{\frac{I_2 + I_3 - I_1}{I_1}} \quad (24)$$

In the embodiment shown in FIGS. 1 and 4, object 9 moves at high speed. This does not mean that the apparatus cannot be applied to the measuring of the thickness of a thin film formed on an object not moving at all. The apparatus of the invention can be used to measure the thickness of any film of semiconductor devices or electronic devices. In other words, the apparatus can be employed as a high-speed, low-cost, film thickness-measuring apparatus in the semiconductor and electronic industries.

The apparatus shown in FIGS. 1 and 4 can accurately measure thickness d of oil film 9b provided that the refractive index of steel plate 9a remains unchanged and has a relative smooth surface. When the refractive index or the surface roughness of plate 9a varies as steel plate 9a is moved, the variation of refractive index or the surface roughness of plate 9a inevitably influences ellipsometric parameters $\psi$ and $\Delta$. Consequently, the apparatus cannot accurately measure the thickness of oil film 9b.

Figure 8:
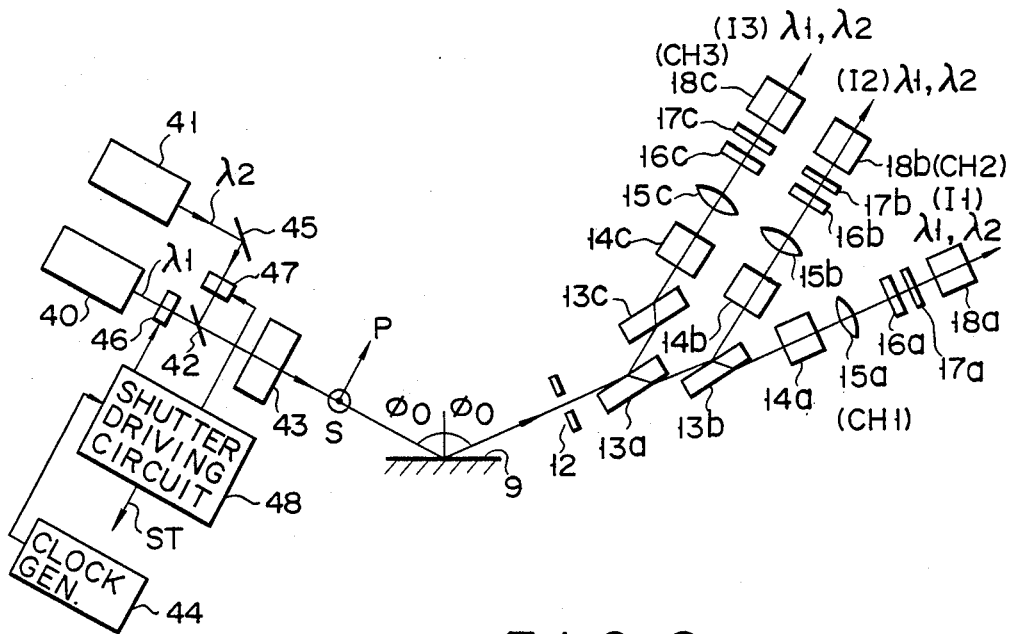
FIG. 8 is a block diagram showing the optical system used in a third embodiment of this invention.
Figure 9:
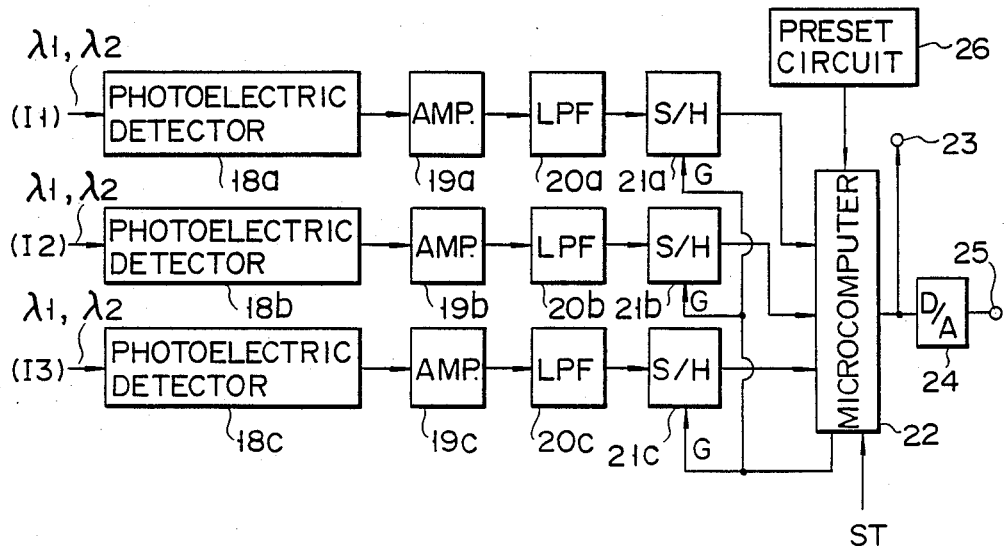
FIG. 9 is a block diagram illustrating the electric circuit used in the third embodiment.

FIGS. 8 and 9 show a second embodiment of the invention, which can obtain correct ellipsometric parameters $\psi$ and $\Delta$, and can thus accurately measure thickness d of oil film 9b even if the refractive index or the surface roughness of steel plate 9a changes while plate 9a is moving. The second embodiment has means for applying to oil film 9b two linearly polarized light beams having different wavelengths. It also has means for receiving the light beams reflected from steel plate 9a coated with oil film 9b, and calculating the thickness of oil film 9b from the relationship between the phase-cosine of the light reflected from steel plate 9a coated with oil film 9b, for the two light beams with different wavelengths. The relationship, from which the thickness of film 9b is obtained, is the difference between these phase-cosine values, for example.

Before describing the structure of the apparatus shown in FIGS. 8 and 9, the experiment conducted by the inventors hereof to invent this second embodiment will be explained.

(1) Two light beams having different wavelengths $\lambda_1$ and $\lambda_2$ were polarized into linearly polarized light beams. The polarized light beams were applied to a tin-plated steel plate at the same incidence angle. The respective light beams reflected from the surface of the steel plate had an elliptical cross section. Phase cosines $\cos\Delta\lambda_{1,s}$ and $\cos\Delta\lambda_{2,s}$ of the reflected light beams changed in proportion to the slight change in the surface roughness or refractive index of the steel plate. That is:

$$\cos\Delta\lambda_{2,s} = \cos\Delta\lambda_{1,s} - m \quad (25)$$

where l and m are constants determined by wavelengths $\lambda_1$ and $\lambda_2$. In this experiment, wavelengths $\lambda_1$ and $\lambda_2$ were 633 nm and 514 nm, respectively. Phase-cosine $\cos\Delta\lambda_{1,s}$ for the light ray having wavelength $\lambda_1$ and phase-cosine $\cos\Delta\lambda_{2,s}$ for the light ray having wavelength $\lambda_2$ changed in proportion to each other, as the surface roughness or refractive index of the steel plate varied slightly, as can be understood from the graph of FIG. 10.

(2) As far as a transparent film having thickness of hundreds of angstroms or less and coated on a flat object was concerned, the difference between the phase-cosine of the light beam having wavelength $\lambda_1$ and reflected from the film on the substrate and the phase-cosine of the light beam having the same wavelength and reflected from the substrate without film was proportionate to the thickness d of the film. The same held true in the case of the light beam having wavelength $\lambda_2$. Namely:

$$d = k_1(\cos\Delta\lambda_1 - \cos\Delta\lambda_{1,s}) \quad (26)$$

$$d = k_2(\cos\Delta\lambda_2 - \cos\Delta\lambda_{2,s}) \quad (27)$$

where $k_1$ is the proportional coefficient for wavelength $\lambda_1$, and $k_2$ is the proportional coefficient for wavelength $\lambda_2$. These coefficients $k_1$ and $k_2$ are constants determined by the incidence angle $\phi_0$ of the linearly polarized light beam applied to the transparent film and by the properties of the film whose thickness d will be measured. More precisely, coefficients $k_1$ and $k_2$ can be regarded as being constant, provided that the complex refractive index $N_2$ of the substrate changes by $\pm 10\%$ or less as is represented by the following relation:

$$|N_2 - \overline{N_2}| \leq 0.1|\overline{N_2}| \qquad (28)$$

Calculations were performed in accordance with equation (3), thereby ascertaining that equations (26) and (27) were true. FIG. 11 is a graph showing the relationship between thickness d and the difference between phase-cosine $\cos\Delta\lambda$ and phase-cosine $\cos\Delta\lambda_s$, that is ($\cos\Delta\lambda - \cos\Delta\lambda_s$) which is obtained from equations (26) and (27) for wavelength $\lambda_1$ of 633 nm and wavelength $\lambda_2$ of 514 nm. As may be understood from FIG. 11, the difference between the phase-cosine of the light reflected from the thin film on the substrate and the phase-cosine of the light reflected from the substrate without film is proportionate to the thickness d of the film. It follows that thickness d can be accurately measured from equations (25), (26) and (27), even if the refractive index or the surface roughness of the substrate changes. That is:

$$d = \frac{k_1 k_2}{k_1 - k_2 l}(\cos\Delta\lambda_2 - l\cos\Delta\lambda_1 + m) \qquad (29)$$
$$= A\cos\Delta\lambda_2 + B\cos\Delta\lambda_1 + C$$

where A, B and C are constants which can be experimentally determined once incidence angle $\phi_0$ has been set.

The structure of the apparatus shown in FIGS. 8 and 9, which is the second embodiment of the invention, will now be described. FIG. 8 schematically illustrates the optical system of the second embodiment. The optical system includes two light sources 40 and 41. Light source 40 emits a collimated monochromatic ray having wavelength $\lambda_1$, and light source 41 emits a collimated ray having wavelength $\lambda_2$. The ray emitted from light source 40 passes semi-transparent mirror 42 and polarized by polarizer 43 into a polarized ray. This polarized ray is applied to the surface of object 9 at incidence angle of $\phi_0$. The ray emitted from light source 41 is reflected by reflector 45 and also by semi-transparent mirror 42, and then polarized by polarizer 43 into a polarized ray. This ray is also applied to object 9 at the same incidence angle of $\phi_0$. Shutter 46 is provided between light source 40 and semi-transparent mirror 42, and shutter 47 is provided between light source 41 and semi-transparent mirror 42. These shutters 46 and 47 are driven by shutter-driving circuit 48, and thus are opened and closed. Shutter-driving circuit 48 generates shutter drive signals ST, which are supplied to microcomputer 22.

The light-receiving section of the optical system shown in FIG. 8 is identical to that of the optical system shown in FIG. 1. The same components as those of the section shown in FIG. 1 are designated by the same numerals in FIG. 8, and will not be described in detail.

FIG. 9 shows the signal-processing section of the second embodiment. This section is also identical to the signal-processing section of the first embodiment. Microcomputer 22 receives the output signals of S/H circuits 21a, 21b and 21c in response to shutter drive signals ST supplied from shutter-driving circuit 48. Microcomputer 22 processes these signals, thereby obtaining phase-cosine $\cos\Delta\lambda_1$ for the polarized ray having wavelength $\lambda_1$ and also phase-cosine $\cos\Delta\lambda_2$ for the polarized ray having wavelength $\lambda_2$, and then calculate thickness d from the phase cosines thus obtained. The digital data showing thickness d is output via output terminal 23, and also input to D/A converter 24. D/A converter 24 converts the digital data to analog data. The analog data is input from terminal 25 to a chart recorder (not shown).

The operation of the second embodiment will now be explained. Shutter-driving circuit 48 opens one of two shutters 46 and 47, while closing the other of these shutters 46 and 47. More specifically, clock generator 44 generates two clock signals CL1 and CL2 which are 180° out of phase with each other, as is illustrated in FIGS. 12(a) and 12(b). Here, two acoustic optical modulator are used as two optical shutters. Clock signals CL1 and CL2 are supplied to shutter-driving circuit 48. Circuit 48 supplies clock signal CL1 to shutter 46, and clock signal CL2 to shutter 47, whereby shutters 46 and 47 are alternately opened and closed. When shutter 46 is opened by clock signal CL1, the Helium-Ne on laser beam of wavelength $\lambda_1$ emitted from light source 40 is applied to object 9 via semi-transparent mirror 42 and polarizer 43, reflected from object 9, and split into three beams by optical flats 13a, 13b and 13c. These beams are applied to photoelectric detectors 18a, 18b and 18c. When shutter 47 is opened by clock signal CL2, the Argon laser beam of wavelength $\lambda_2$ emitted from light source 41 is applied to object 9 after it has been reflected by semi-transparent mirror 42 and passed through polarizer 43. The polarized Argon laser beam is reflected from object 9 and split into three beams by optical flats 13a, 13b and 13c. The three beams are applied to photoelectric detectors 18a, 18b and 18c.

Photoelectric detectors 18a, 18b and 18c generate electric signals representing $(I_1)\lambda_1,\lambda_2$ $(I_2)\lambda_1,\lambda_2$ and $(I_3)\lambda_1,\lambda_2$. The three electric signals are amplified by amplifiers 19a, 19b and 19c, sampled and held by S/H circuits 21a, 21b and 21c, and finally input to microcomputer 22. Microcomputer 22 processes these input signals, thereby calculating phase-cosine $\Delta\lambda_1$ and $\Delta\lambda_2$ for wavelengths $\lambda_1$ and $\lambda_2$, as follows:

$$\cos(\Delta\lambda_1 - \Phi_{0\lambda_1}) = \qquad (37)$$

$$\frac{(I_2)\lambda_1 - (I_3)\lambda_1}{2(I_1)\lambda_1} \sqrt{\frac{(I_1)\lambda_1}{(I_2)\lambda_1 + (I_3)\lambda_1 - (I_1)\lambda_1}}$$

$$\cos(\Delta\lambda_2 - \Phi_{0\lambda_2}) = \qquad (38)$$

$$\frac{(I_2)\lambda_2 - (I_3)\lambda_2}{2(I_1)\lambda_2} \sqrt{\frac{(I_1)\lambda_2}{(I_2)\lambda_2 + (I_3)\lambda_2 - (I_1)\lambda_2}}$$

The following equation holds true:

$$(\tan\Psi)\,\lambda_1, \lambda_2 = \qquad (39)$$

$$|\sigma_1 \cdot \sigma_2|\,\lambda_1, \lambda_2 \sqrt{\frac{(I_1)\lambda_1, \lambda_2}{(I_2)\lambda_1, \lambda_2 + (I_3)\lambda_1, \lambda_2 - (I_1)\lambda_1, \lambda_2}}$$

Therefore, ellipsometric parameters $\psi$ and $\Delta$ can be simultaneously obtained by substituting the values for the invariables, $\phi_{0\lambda_1}$, $\lambda_2$ and $|\sigma_1\sigma_2|$ $\lambda_1$, $\lambda_2$. Values $\Phi_{0\lambda_1}$ and $\Phi_{0\lambda_2}$, both being invariables, can be corrected into $\cos\Delta\lambda 1$ and $\cos\Delta\lambda 2$.

Figure 13:
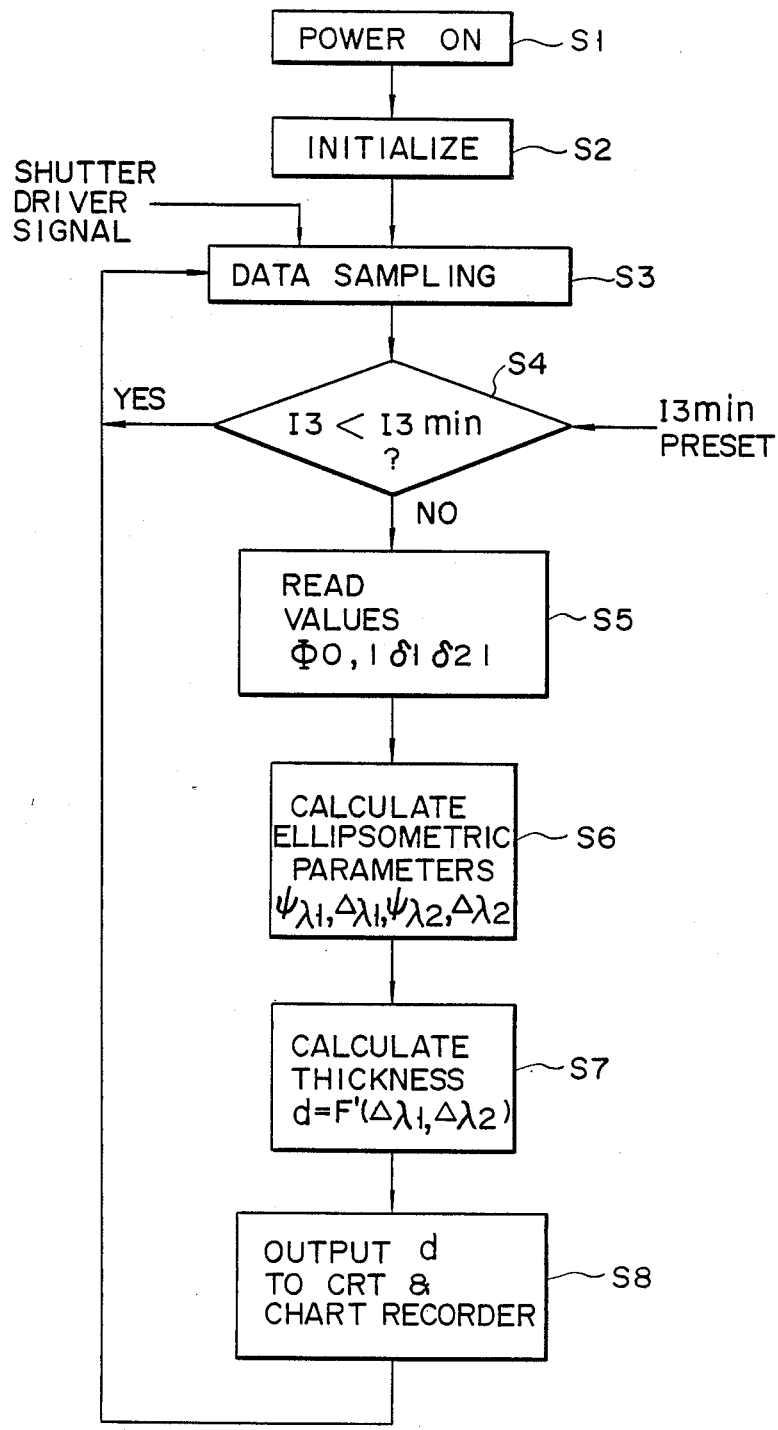
FIG. 13 is a flow chart explaining the steps performed by the embodiment shown in FIG. 9.

FIG. 13 is a flow chart explaining the operation of microcomputer 22 used in the second embodiment shown in FIGS. 8 and 9. The operation is identical to that of the microcomputer used in the first embodiment, except for the step of obtaining data about two different wavelengths $\lambda_1$ and $\lambda_2$. Therefore, it is not described in detail how microcomputer 22 functions in the second embodiment.

Let us assume that object 9 is a steel plate coated with an oil film. Amount M of oil coated on the steel plate is given:

$$M = \delta \times d \quad (40)$$

where $\delta$ is the density of the oil, and d is the thickness of the oil film. As evident from equation (40), amount M and thickness d are proportionate to each other. When polarized beam having wavelength $\lambda_1$ of 633 nm, and a polarized beam having wavelength $\lambda_2$ of 514 nm are applied to object 9 at incidence angle $\phi_0$ of 70°, amount M can be given as follows, provided that coefficients A (82.8), B (−57.7) and C (1.61) in equation (29) have been obtained by experiment:

$$M = 82.8(\cos\Delta\lambda_2 - 0.697\cos\Delta\lambda_1 + 0.0294) \quad (41)$$

Hence, by substituting the actual values for $\cos\Delta\lambda_1$ and $\cos\Delta\lambda_2$, both contained in equation (41), we can obtain amount M of oil coated on the steel plate. FIG. 14 shows the comparison of amount M actually measured by the apparatus and value M measured by the hydrophil balance method which is considered a reliable off-line, oil amount-measuring method. As is evident from FIG. 14, values measured by the apparatus shown in FIGS. 8 and 9 fell within a narrow range corresponding to ±1 mg/m². Obviously, this apparatus according to the present invention can more accurately measure the thickness of a thin film than the conventional apparatus.

The present invention is not limited to the embodiments described above. It can be also applied to the case where the phase-cosines, $\cos\Delta\lambda_1$ and $\cos\Delta\lambda_2$, and the thickness d of the film have more general relationship with wavelengths $\lambda_1$ and $\lambda_2$:

$$\cos\Delta\lambda_1 = f_1(d) + \cos\Delta\lambda_{1,s} \quad (43)$$

$$\cos\Delta\lambda_2 = f_2(d) + \cos\Delta\lambda_{2,s} \quad (44)$$

where the following relation holds within a certain variation range of the substrate properties:

$$\cos\Delta\lambda_{2,s} = f_0(\cos\Delta\lambda_{1,s}) \quad (42)$$

where $f_0$ is not necessary to a linear function. Therefore:

$$\cos\Delta\lambda_2 - f_2(d) = f_0\{\cos\Delta\lambda_1 - f_1(d)\} \quad (45)$$

As has been described above, the apparatus of the second embodiment of the present invention can accurately measure the thickness of a thin film coated on an object even if the refractive index of the object and other physical properties thereof continuously change.

What is claimed is:

1. A film thickness-measuring apparatus comprising:
   light-applying means including a polarizer for applying a linearly polarized light beam, having a predetermined polarizing angle, to a film at a predetermined incidence angle in order to measure the thickness of the film;
   beam-splitting means for splitting a light beam reflected from said film into at least three light beams with the same spatial distribution as said reflected beam;
   means for extracting at least three linearly polarized light components of different respective polarizing angles from said at least three light beams, respectively;
   photoelectric conversion means for converting the at least three light components into at least three corresponding electric signals representing the intensities of the respective at least three light components; and
   calculation means for performing predetermined calculations on the at least three electric signals supplied from said photoelectric conversion means to thereby obtain two ellipsometric parameters, an amplitude ratio $\psi$, and phase $\Delta$, and then calculate the thickness of the film from the ellipsometric parameters thus obtained.

2. An apparatus according to claim 1, wherein said beam-splitting means comprises three optical flats made of the same material, having the same shape, positioned parallel to one another, for splitting the light beam reflected from said film, into three light beams, and said extracting means comprises a plurality of analyzing means having different analyzing angles, for passing the light beams supplied from said optical flats.

3. An apparatus according to claim 1, wherein said photoelectric conversion means has lens means for focusing the at least three light components, respectively, at a focal point; aperture means located at the focal point; and photoelectric detector means for generating an electric signal representing the intensity of a respective light component, from said at least three light components, passed through said aperture means.

4. An apparatus according to claim 2, wherein a polarizing angle of said polarizer is $\theta = 45°$, and wherein the analyzing angles of said analyzing means are $a_1 = 0°$, $a_2 = 45°$, $a_3 = -45°$, so that said calculation means calculate the amplitude ratio $\psi$ and said phase $\Delta$ in accordance with the following equations:

$$\cos(\Delta - \Phi_0) = \frac{I_2 - I_3}{2I_1} \sqrt{\frac{I_1}{I_2 + I_3 - I_1}}$$

$$\tan\psi = |\sigma_1 \sigma_2| \sqrt{\frac{I_1}{I_2 + I_3 - I_1}}$$

where $I_1$, $I_2$ and $I_3$ are intensities of the three light beams supplied from said three optical flats, which are represented by the electric signals generated by said photoelectric conversion means, $\nabla_1$ and $\nabla_2$ being reflection coefficient ratios, and $\phi_0$ is a phase difference between phases of ratios $\nabla_1$ and $\nabla_2$.

5. An apparatus according to claim 1, wherein said beam splitting means comprises four optical flats made of the same material, having the same shape, positioned parallel to one another, for splitting the light beam reflected from said film, into three light beams, and said extracting means comprises a plurality of analyzing means having different analyzing angles, for passing the light beams supplied from said optical flats.

6. An apparatus according to claim 3, which has a measuring view the size of which is given as:

$$D \leq 7.0 \times 10^{-3} f$$

where f is the focal distance of said lens means, and D is the diameter of said aperture means.

7. An apparatus according to claim 1, wherein said polarizer of said light-applying means applies at least two linearly polarized light beams having different wavelengths and a predetermined orientation angle, to a film at the same predetermined incidence angle in order to measure the thickness of the film.

* * * * *